US00PP33426P3

(12) United States Plant Patent
Brouwer

(10) Patent No.: US PP33,426 P3
(45) Date of Patent: Aug. 31, 2021

(54) ***SPATHIPHYLLUM* PLANT NAMED 'SP7018'**

(50) Latin Name: ***Spathiphyllum* sp. Schott**
Varietal Denomination: SP7018

(71) Applicant: ISB Holland B.V., Nootdorp (NL)

(72) Inventor: Wim A. J. Brouwer, Nootdorp (NL)

(73) Assignee: ISB Holland B. V., Nootdorp (NL)

( * ) Notice: Subject to any disclaimer, the term of this patent is extended or adjusted under 35 U.S.C. 154(b) by 0 days.

(21) Appl. No.: 17/092,242

(22) Filed: Nov. 7, 2020

(65) Prior Publication Data

US 2021/0168982 P1 Jun. 3, 2021

(30) Foreign Application Priority Data

Nov. 30, 2019 (EP) ..... 20193276

(51) Int. Cl.
*A01H 5/12* (2018.01)
*A01H 6/10* (2018.01)

(52) U.S. Cl.
USPC ..... Plt./364

(58) Field of Classification Search
USPC ..... Plt./364
See application file for complete search history.

*Primary Examiner* — Susan McCormick Ewoldt
(74) *Attorney, Agent, or Firm* — Samuel R. McCoy, Jr.

(57) ABSTRACT

'SP7018' is a new and distinctive variety of *Spathiphyllum* plant which is characterized by a compact, densely-foliaged growth habit which is suitable for production in relatively small nursery containers, thin foliage which is soft to the touch, uniquely variegated foliage, and the stability of all characteristics from generation to generation.

3 Drawing Sheets

Latin name of the genus and species: The Latin name of the genus and species of the novel variety disclosed herein is *Spathiphyllum* sp. Schott.

Variety denomination: The inventive variety of *Spathiphyllum* disclosed herein has been given the variety denomination 'SP7018'.

CROSS REFERENCE TO RELATED APPLICATIONS

This application claims priority to the Community Plant Variety Rights application number 2019/3276, Nov. 20, 2019, which is herein incorporated by reference.

BACKGROUND OF THE INVENTION

Parentage: The new plant is a seedling selection which resulted from the controlled pollination of the proprietary seed parent, *Spathiphyllum* sp. '6527' (not patented), and the proprietary pollen parent, *Spathiphyllum* sp. '6578' (not patented). Both parents, which exhibited a compact habit and non-variegated foliage, were developed and owned by the inventor and were never commercially released. Said cross was performed by the inventor at a commercial greenhouse in Nootdorp, The Netherlands in August of 2013. Seeds from said cross were harvested, then germinated, and the resulting seedlings were grown to a mature size in order to evaluate for desirable commercial characteristics. In September of 2014, the inventor selected the instant *Spathiphyllum* plant for commercialization due to its compact, densely-foliaged growth habit. The new plant was given the variety denomination 'SP7018'.

Asexual Reproduction: Asexual reproduction of 'SP7018', by way of meristematic tissue culture, was first performed in October of 2014 at a commercial laboratory in Evergem, Belgium. Nine successive generations so produced have shown that the unique features of the instant cultivar are stable and reproduced true to type.

SUMMARY OF THE INVENTION

The cultivar 'SP7018' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Spathiphyllum* plant, 'SP7018'. These traits, in combination, distinguish 'SP7018' as a new and distinct cultivar:

1. *Spathiphyllum* 'SP7018' exhibits a compact, densely-foliaged growth habit which is suitable for production in relatively small nursery containers;
2. *Spathiphyllum* 'SP7018' exhibits thin foliage which is soft to the touch; and
3. *Spathiphyllum* 'SP7018' exhibits uniquely variegated foliage that is irregularly mottled and streaked with a combination of white, green-white and greyed-green in a pattern that follows the secondary veins.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
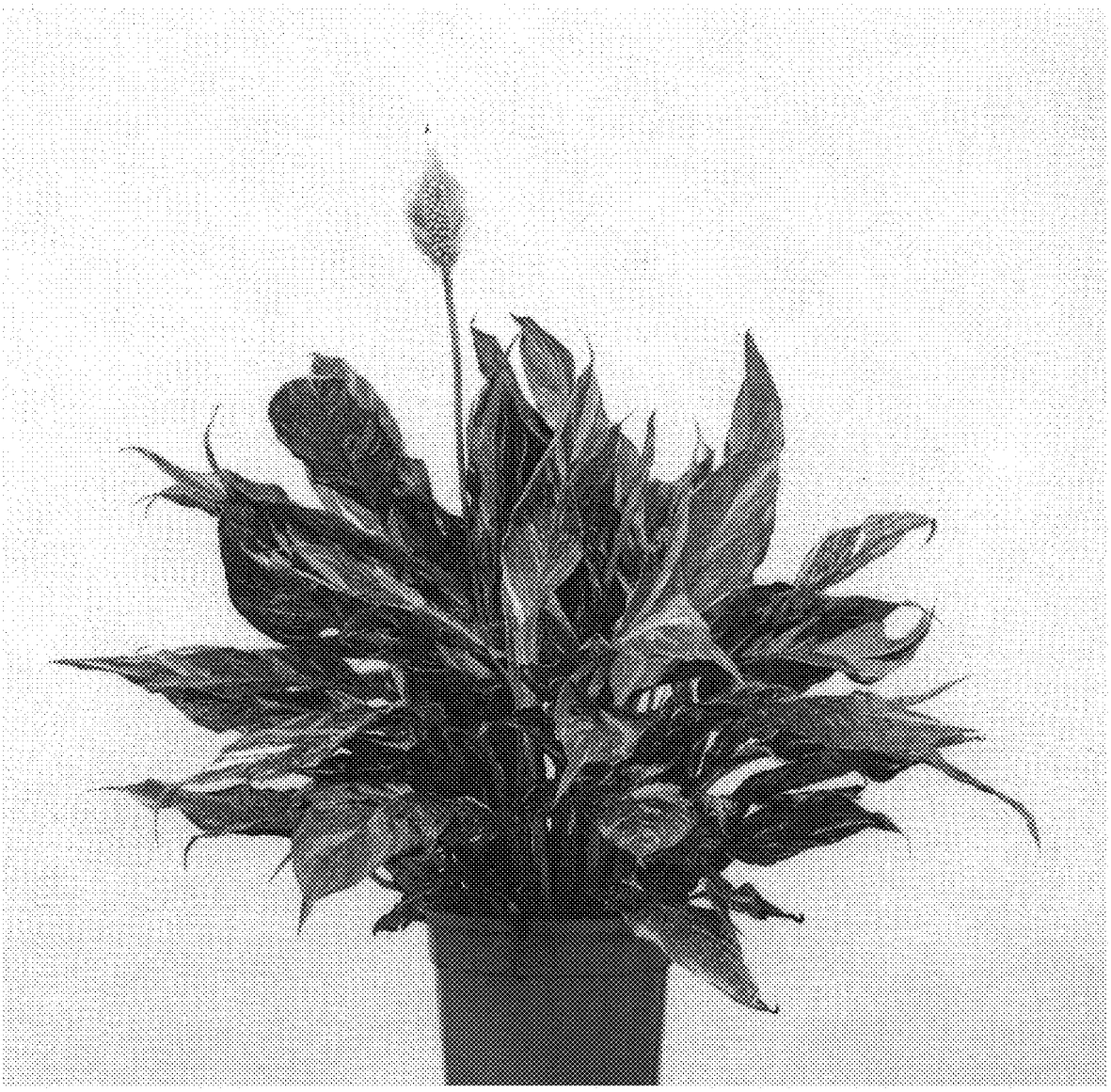
FIG. 1 shows, as nearly true as it is reasonably possible to make the same in color illustrations of this type, an exemplary 'SP7018' plant. The plant shown is approximately 12 months old from a rooted cutting, potted into a 17 cm nursery pot, grown in a climate-controlled greenhouse in Roelofarendsveen, the Netherlands.
Figure 2:
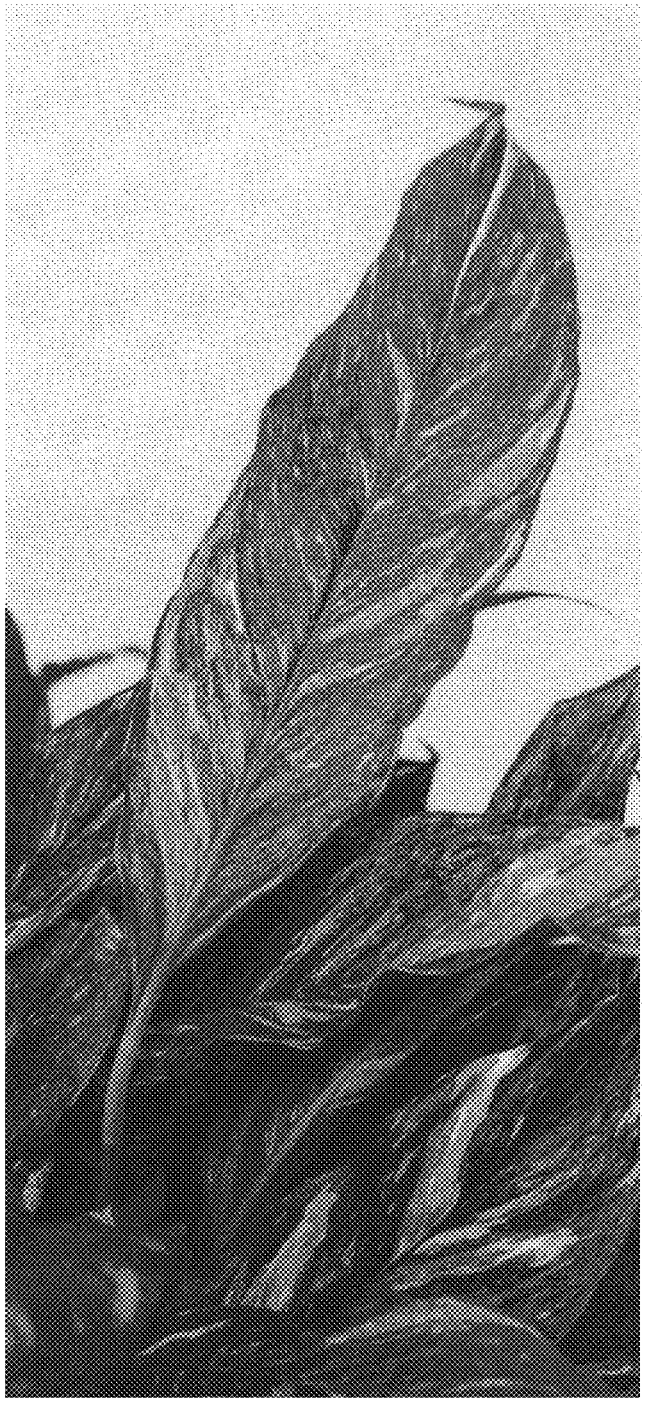
FIG. 2 shows, as nearly true as it is reasonably possible to make the same in color illustrations of this type, the typical foliage of the plant in FIG. 1.
Figure 3:
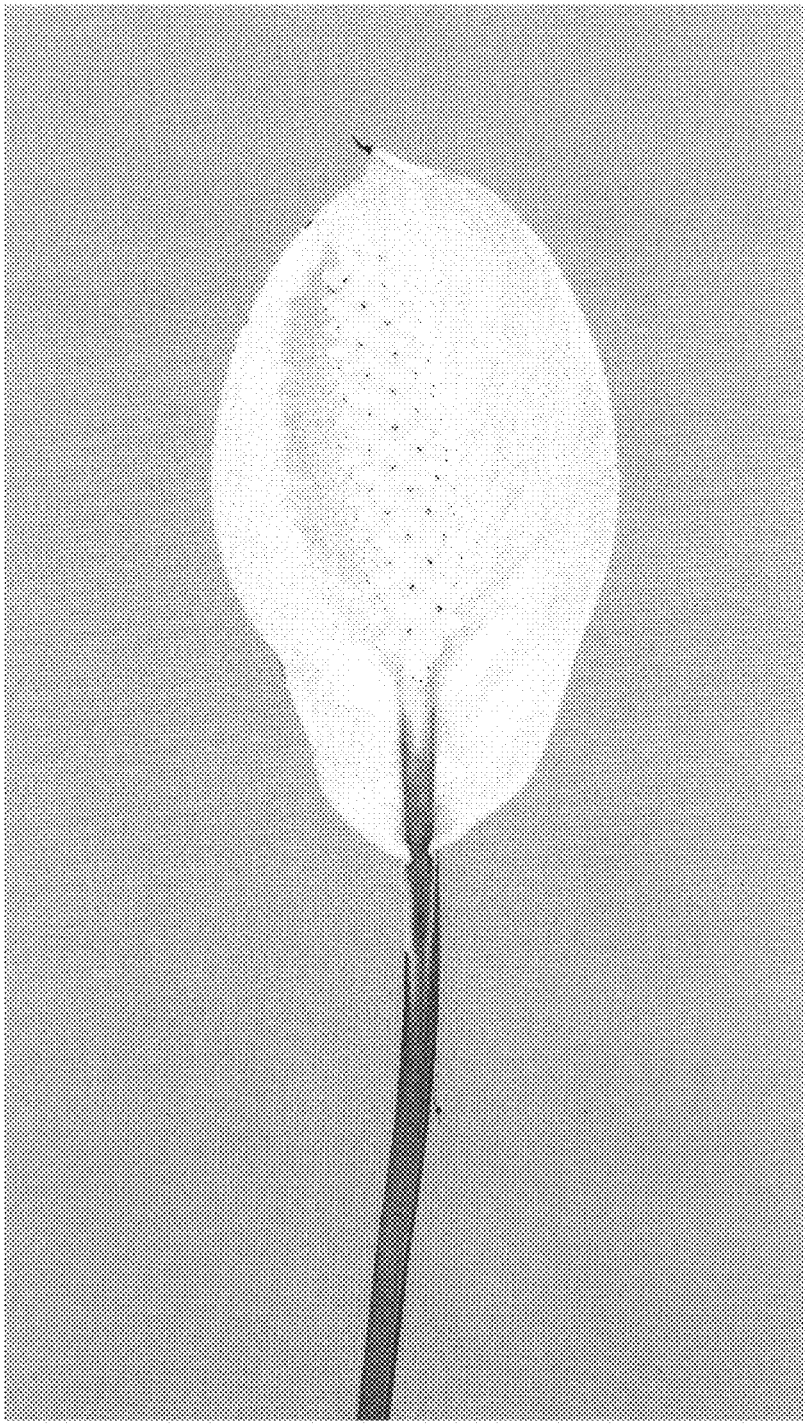
FIG. 3 shows, as nearly true as it is reasonably possible to make the same in color illustrations of this type, the typical flower of the plant in FIG. 1.

The following observations and measurements made in September of 2020 describe averages from a sample set of six specimens of 1 year old 'SP7018' plants grown in 14 cm nursery containers at commercial greenhouse in Apopka, Fla. Plants were produced using conventional greenhouse production protocols for *Spathiphyllum*. Temperatures ranged from 18 to 22 degrees Celsius, both night and day. No chemical pest and disease control measures were taken. No photoperiodic treatments or artificial light was given to the plants.

Those skilled in the art will appreciate that certain characteristics will vary with older or, conversely, with younger plants. 'SP7018' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'SP7018' and comparisons with the parents and the most similar variety of common knowledge are provided below.

General plant description:

*Growth habit*.—Clumping herbaceous perennial; broad spreading to upright with foliage arising directly from the base of each clump.

*Plant profile*.—Near globular with inflorescences carried slightly above the foliage.

*Height*.—38.2 cm in height, to the highest leaf; 50.8 cm to top of highest spathe.

*Width*.—Average 61.8 cm in width.

*Growth rate*.—Moderately fast growing.

*Plant vigor*.—Moderately to highly vigorous.

*Propagation*.—Method — Meristematic tissue culture. Time to initiate roots — Approximately 18 days to initiate roots at an approximate soil temperature of 25 degrees Celsius. Crop time — Approximately 14 weeks to produce a well-rooted cutting at an approximate soil temperature of 20 to 30 degrees Celsius.

*Environmental tolerances*.—Moderately high tolerance to rain and wind; tolerant of temperatures ranging from 5 to 40 degrees Celsius. Cold hardy to USDA Hardiness Zone 10.

*Pest resistance and susceptibility*.—Plants have not been observed to be any more or less susceptible or resistant to pathogens and pests common to *Spathiphyllum*.

Root system:

*General*.—Thick, fleshy roots with fine, fibrous lateral roots.

*Distribution in the soil profile*.—Shallow to moderately deep.

*Texture*.—Smooth; glabrous.

*Color*.—Orange-white, nearest to RHS 158C.

Stems:

*Branching characteristics*.—Clumping plant with leaves emerging directly from the base of the plant; no lateral branching.

Foliage:

*Arrangement*.—Alternate; equitant.

*Division*.—Simple.

*Attachment*.—Petiolate.

*Quantity of leaves per shoot*.—Average of 5.

*Quantity of shoots per plant*.—Average of 17.

*Quantity of leaves per plant*.—Approximately 85.

*Lamina*.—Shape — Narrow ovate to narrow elliptic. Apex — Narrow apiculate. Base — Attenuate. Aspect — Very slightly carinate; occasionally reflexed; occasionally spiraled. Attitude — Younger foliage at the center of the plant is held upright; older foliage is more relaxed. Dimensions — 32.1 cm long and 7.3 cm wide. Margin — Entire; moderately undulate. Texture and luster, adaxial surface — Moderately rugose, glabrous, and very slightly glossy. Texture and luster, abaxial surface — Moderately rugose, glabrous, and slightly glossy. Juvenile color, adaxial surface — A mixture of green and yellow-green, nearest to RHS 137A, 143A, 143B and 144A; heavily, irregularly mottled and streaked with a combination of green-white and greyed-green in a pattern that follows the secondary veins, nearest to RHS 157A, 157B, 157C, 157D, 193B, 193C and 193D. Juvenile color, abaxial surface — Green, nearest to a mixture of RHS 137C, 137D, 138A, 143B and 143C; heavily, irregularly mottled and streaked with a combination of white, green-white and greyed-green in a pattern that follows the secondary veins, nearest to RHS 155C, 157C, 157D, 188A, 188B, 189A, 189B, 189C and 189D. Mature color, adaxial surface — Green, nearest to RHS 137A; heavily, irregularly mottled and streaked with a combination of white, green-white and greyed-green in a pattern that follows the secondary veins, nearest to RHS 155D, 157D, 188A, 188B, 189A, 189B, 189C and 189D. Mature color, abaxial surface — Yellow-green, nearest to RHS 147B. Venation — Vein pattern — Pinnate. Vein color, adaxial surface — Green, nearest to RHS NN137B, and axially striped yellow-green, nearest to RHS 150C. Vein color, abaxial surface — Yellow-green, nearest to RHS 144B, and axially striped with a lighter shade of yellow-green, nearest to RHS 145B.

*Petiole, including geniculum*.—Length — Approximately 17.0 cm. Width — 0.7 cm, proximally; 0.4 cm distally. Texture and luster — Smooth, glabrous, and very slight glossy. Strength — Strong. Color, adaxial surface — Yellow-green, nearest to RHS 147D. Color, abaxial surface — Green, nearest to RHS 143A, and axially striped greyed-green, nearest to RHS 193A. Geniculum — Length — Approximately 2.9 cm. Width — Approximately 0.45 cm. Texture and Luster — Smooth, glabrous and matte. Color — Nearest to in between green and yellow, RHS 138A and 147B; axially striped lighter yellow-green, nearest to RHS 147D. Petiole wings — Length — Approximately 13.2 cm. Width — Approximately 0.6 cm. Color, adaxial surface — Green, nearest to a mixture of RHS 137B and 137C; axially striped yellow-green, nearest to RHS 154D.

Color, abaxial surface — Green, nearest to RHS 137B; axially striped yellow-green, nearest to a mixture of RHS 154C and 154D.

Inflorescence:

*Type*.—Spadix.

*Arrangement*.—Peduncles arise directly from the base of the plant with spadices carried slightly above the foliar plane.

*Attitude*.—Approximately 20 degrees from vertical.

*Dimensions*.—11.4 cm long, excluding the peduncle, and 5.8 cm wide; spathe is 3.0 cm deep.

*Flowering habit*.—Continuous.

*Quantity of spathes per plant*.—1.

*Natural flowering season*.—Autumn into spring in the Netherlands, with occasional flowering in summer.

*Time to flowering*.—24 weeks from planting.

*Fragrance*.—Faint, sweet and pleasant fragrance, typical of *Spathiphyllum* sp.

*Self-cleaning or persistent*.—Persistent.

*Flower longevity*.—Flowers stay in good condition approximately 3 weeks on the plant.

*Peduncle*.—Attitude — Approximately 10 degrees from vertical. Length — 41.8 cm. Diameter — 0.4 cm. Strength — Strong. Texture and luster — Smooth, glabrous and very slightly glossy. Color — Yellow-green, nearest to RHS 144A, and axially striped lighter, nearest to RHS 150C.

Spathe:

*Attitude*.—Approximately 20 degrees from vertical.

*Aspect*.—Moderately concave.

*Length*.—11.4 cm.

*Width*.—5.8 cm.

*Depth*.—3.0 cm.

*Shape*.—Elliptic to ovate.

*Margin*.—Entire; very slightly coarsely undulate.

*Apex*.—Apiculate.

*Base*.—Obtuse.

*Texture, inner and outer surfaces*.—Glabrous, slightly coriaceous.

*Luster, inner and outer surfaces*.—Inner surface is slightly glossy; outer surface is very slightly glossy.

*Color*.—Inner surface, when opening — White, nearest to RHS 155C, and centrally suffused with yellow-green, nearest to RHS 144A. Outer surface, when opening — White, nearest to RHS 155C. Inner surface, at maturity — White, nearest to RHS NN155A. Outer surface, at maturity — White, nearest to RHS NN155B; main vein is greyed-green, nearest to RHS 196D. Fading to — Not fading.

Spadix:

*Attitude*.—At an average angle of 20 degrees to the peduncle.

*Shape*.—Oblong, columnar.

*Apex*.—Obtuse.

*Base*.—Obtuse.

*Length*.—Approximately 6.0 cm.

*Width*.—Approximately 1.5 cm.

*Color*.—When opening — Yellow-white, nearest to RHS 158C. Mature — Yellow-white, nearest to a mixture of RHS 158B and 158C.

*Flowers*.—General — Flowers are greatly diminished, to the point of being largely indistinguishable and immeasurable. Quantity of flowers per spadix — Approximately 180. Arrangement — Spirally placed on spadix. Shape — Rounded. Diameter — Approximately 0.35 cm. Height — Approximately 0.3 cm.

Reproductive organs:

*General*.—Reproductive organs are greatly diminished, to the point of being largely indistinguishable and immeasurable.

*Anthers*.—Color — Yellow-white, nearest to RHS 158C.

*Pollen, amount*.—Sparse.

*Pollen color*.—White, nearest to RHS 155A.

*Stigma*.—Quantity — 1. Shape — Conical to pyramid-shaped. Dimensions — 0.3 cm tall and 0.05 cm in diameter. Color — Greyed-yellow, nearest to RHS 160D.

*Ovary color*.—Yellow-white, nearest to RHS 158C.

Seed and fruit: Seed production has not been observed.

Comparisons With the Parent

Plants of the new cultivar 'SP7018' may be distinguished from the seed parent, *Spathiphyllum* sp. '6527' (not patented), by the following combination of characteristics described in Table 1.

TABLE 1

| Characteristic | 'SP7018' | '6527' |
|---|---|---|
| Foliage shape. | Narrow ovate to narrow elliptic. | Ovate. |
| Foliar margins. | Moderately undulate. | Undulate. |
| Foliage variegation. | Present. | Absent. |

Plants of the new cultivar 'SP7018' may be distinguished from the pollen parent, *Spathiphyllum* sp. '6578' (not patented) by the following combination of characteristics described in Table 2.

TABLE 2

| Characteristic | 'SP7018' | '6578' |
|---|---|---|
| Foliage variegation. | Present. | Absent. |
| Foliage shape. | Narrow ovate to narrow elliptic. | Ovate. |
| General coloration of the mature adaxial foliar surface. | Green and heavily, irregularly mottled and streaked with a combination of white, green-white and greyed-green. | Green. |

Comparisons With the Most Similar Variety of Common Knowledge

Plants of the new cultivar 'SP7018' may be distinguished from the commercial variety, *Spathiphyllum* sp. '500JET' (U.S. Plant Pat. No. 25,201), by the following combination of characteristics described in Table 3.

TABLE 3

| Characteristic | 'SP7018' | '500JET' |
|---|---|---|
| Foliage variegation. | Present. | Absent. |
| Foliage shape | Narrow ovate to narrow elliptic. | Ovate to narrow ovate. |

TABLE 3-continued

| Characteristic | 'SP7018' | '500JET' |
|---|---|---|
| Foliage texture. | Moderately rugose. | Smooth. |
| Foliar margins. | Moderately coarsely undulate. | Moderately finely undulate. |
| General coloration of the juvenile adaxial foliar surface. | A mixture of green and yellow green; heavily, irregularly mottled and streaked with a combination of white, green-white and greyed-green. | Yellow-green. |
| General coloration of the mature adaxial foliar surface. | Green and heavily, irregularly mottled and streaked with a combination of white, green-white and greyed-green. | Yellow-green. |

TABLE 3-continued

| Characteristic | 'SP7018' | '500JET' |
|---|---|---|
| General coloration of the main vein on the adaxial foliar surface. | Green and axially striped yellow-green. | In between green and yellow-green. |
| General coloration of the main vein on the abaxial foliar surface. | Yellow-green and axially striped with a lighter shade of yellow-green. | Yellow-green. |
| General coloration of the abaxial petiole surface. | Green and axially striped greyed-green. | Green. |
| General coloration of the petiole wing. | Green and axially striped yellow-green. | Yellow-green. |
| General coloration of the petiole wing. | Green and axially striped yellow-green. | Yellow-green. |

That which is claimed is:

1. A new and distinct variety of *Spathiphyllum* plant named 'SP7018', substantially as described and illustrated herein.

* * * * *